United States Patent [19]

Kanematsu et al.

[11] Patent Number: 5,219,861

[45] Date of Patent: Jun. 15, 1993

[54] 6 β-THIOMORPHINE DERIVATIVES

[75] Inventors: Ken Kanematsu, Fukuoka; Issei Takayanagi, Chiba; Mitsutaka Yoshida, Shizuoka, all of Japan

[73] Assignee: Chugai Seiyaku Kabushiki Kaisha, Tokyo, Japan

[21] Appl. No.: 712,760

[22] Filed: Jun. 10, 1991

Related U.S. Application Data

[63] Continuation-in-part of Ser. No. 454,251, Dec. 21, 1989, abandoned.

[30] Foreign Application Priority Data

Dec. 21, 1988 [JP] Japan .................. 63-322729

[51] Int. Cl.$^5$ .................. A61K 31/485; C07D 489/00
[52] U.S. Cl. ...................... 514/282; 546/44
[58] Field of Search .................. 514/282; 546/44

[56] References Cited

FOREIGN PATENT DOCUMENTS 0149788 6/1989 Japan .................. 546/44

OTHER PUBLICATIONS

*Journal of Medicinal Chemistry*, "Some Potent Mosphine Antagonists Possessing High Analgesic Activity", M. Gates et al., vol. 7, No. 2, pp. 127–131, (Mar. 1964).

*Chemical Abstracts*, vol. 109, No. 21, (Nov. 1988), p. 49, Column 1, abstract No. 183385r, Takayanagi et al.

*Chemical and Pharaceutical Bulletin*, "Design and Synthesis of Sulfur-Containing Morphine and an Opioid Receptor Probe", vol. 36, No. 6, (1988), pp. 2282–2285, Fujii et al.

*Chemical Abstracts*, vol. 70, No. 19, (May 1969), p. 367, column 2, abstract No. 88020k, Bognar et al.

Takayanagi et al., Arch. Int. Pharmacodyn. Ther. 1988, vol. 294, pp. 71–84 (1988).

Burger's Medicinal Chemistry, 4th ed., Wolff, ed., John Wiley & Sons, New York, A Wiley-Interscience publication 1981, pp. 711–712.

Takayanagi et al., Gen. Pharmac., vol. 21, No. 5, pp. 605–611 (1990), Chemical Abstracts vol. 113; 204260w (1990).

Takayanagi et al., Gen. Pharmac. 1990, 21(4) pp. 541–546 Chemical Abstracts, vol. 113:109138d (1990).

*Primary Examiner*—Donald G. Daus
*Attorney, Agent, or Firm*—Browdy and Neimark

[57] ABSTRACT

A novel morphine derivative represented by the following general formula:

wherein
$R_1$ represents a hydrogen atom, a lower alkyl group or a lower alkanoyl group;
$R_2$ represents a hydrogen atom, a lower alkylthio group, an aryl group, a lower alkoxycarbonylalkyl group, a lower alkyl group or a lower alkanoyl group;
$R_3$ represents a lower cycloalkylmethyl group or an allyl group, and a pharmaceutically acceptable acid addition salt thereof. The compound of the above general formula shows an analgesic activity 5 or more times as high as that of morphine and a narcotic antagonist action. Further, it exhibits an extremely low drug dependence. These properties make it highly useful as an active ingredient of drugs such as analgesics or anesthetics.

11 Claims, 1 Drawing Sheet

ANALGESIC EXAMINATION ON MICE BY RADIANT HEAT–STIMULATION TEST (MEAN OF 7 ANIMALS ± S.E.) ** : P<0.01 (DUNNETT'S TEST)

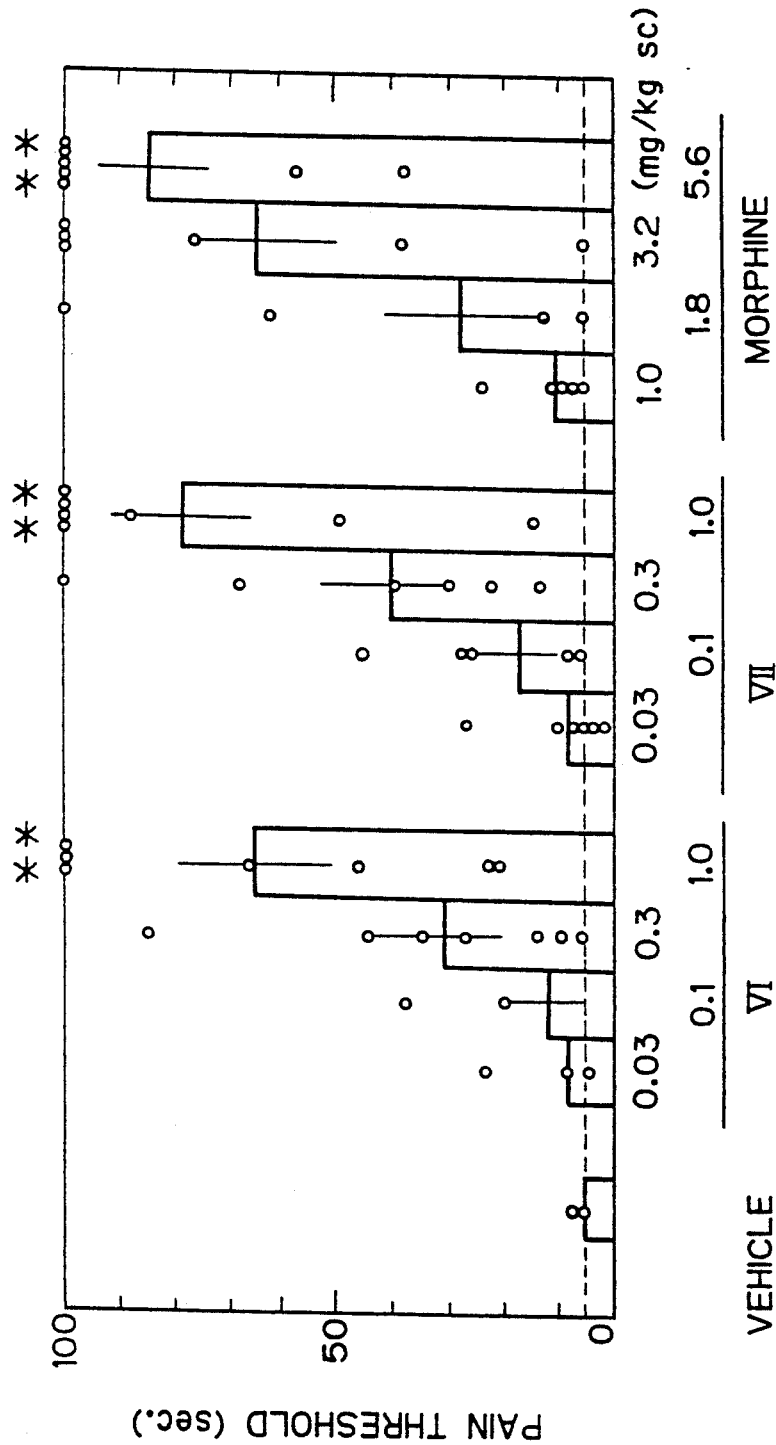

6 β-THIOMORPHINE DERIVATIVES

This application is a continuation-in-part of co-pending Ser. No. 07/454,251, filed on Dec. 21, 1989 now abandoned, the contents of which are hereby incorporated by reference herein.

FIELD OF INVENTION

This invention relates to a novel 6β-thiomorphine derivative represented by the following general formula (I):

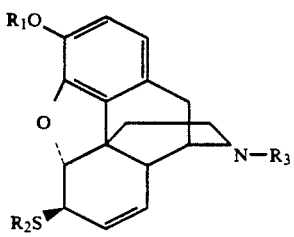

wherein
$R_1$ represents a hydrogen atom, a lower alkyl group or a lower alkanoyl group;
$R_2$ represents a hydrogen atom, a lower alkylthio group, an aryl group, a lower alkoxycarbonylalkyl group, a lower alkyl group or a lower alkanoyl group; and
$R_3$ represents a lower cycloalkylmethyl or an allyl group.

The compound represented by the general formula (I) is expected to be useful as a drug such as a highly effective nonnarcotic analgesic, since it exhibits high analgesic and narcotic antagonist actions and yet an extremely low drug dependence.

BACKGROUND OF THE INVENTION

Morphine, which is known as the major component of opium alkaloids, has been frequently used in drugs such as anesthetics and analgesics. However, it is disadvantageous in that it causes drug dependence and is liable to cause morphinomania.

It is known that naloxone represented by the following formula (II):

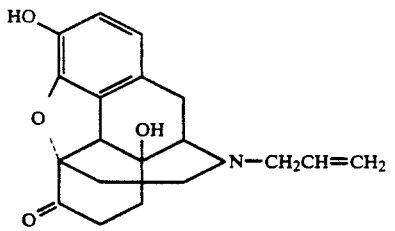

shows a narcotic antagonist action, similar to the compound of the present invention. However, naloxone has only a slight analgesic action, which does not make it particularly suitable as an analgesic. Thus, there has been an urgent demand for a drug which has potent analgesic and narcotic antagonist actions and yet exhibits low drug dependence.

SUMMARY OF THE INVENTION

The present inventors have conducted extensive studies in order to solve the aforesaid problems. As a result, they have found out that a compound represented by the general formula (I) is superior in analgesic activity to morphine, shows narcotic antagonism and exerts excellent effects as a medicine when orally administered, thus completing the present invention.

Accordingly, the present invention provides a 6β-thiomorphine derivative represented by the general formula (I).

BRIEF DESCRIPTION OF THE DRAWING

FIG. 1 shows the result of an analgesic examination on the compounds of the present invention and morphine hydrochloride effected by radiant heat-stimulation test using mice.

DETAILED DESCRIPTION OF THE PREFERRED EMBODIMENTS

The 6β-thiomorphine derivative of the present invention, wherein $R_3$ is a lower cyclopropylmethyl group, may be obtained by, for example, the following process. Namely, cycloalkylmethylnormorphine is obtained from normorphine of the formula (III) in accordance with the method of Gates and Montzka [refer to M. Gates, T. A. Montzka; J. Med. Chem., 7, 127 (1964)]. Next, the obtained compound is converted into a ditosylate of the general formula (VI) by a conventional method and then reacted with a compound represented by the general formula $R_5SX$, wherein $R_5$ represents a lower alkyl group, a lower alkylthio group, an aryl group, a lower alkoxycarbonylalkyl group or a hydrogen atom; and X represents an alkali metal, to thereby give a compound of the general formula (VII). The compound (VII) is then hydrolyzed and acylated or alkylated at the 3-position by a conventional method, if required, to thereby give the target compound.

Examples of the lower alkanoyl groups of $R_1$ and $R_2$ of the compound of the present invention include those having 2 to 7 carbon atoms. Preferable examples thereof include acetyl and propionyl groups. Examples of the lower alkylthio group $R_2$ include those having 1 to 6 carbon atoms. Preferable examples thereof include methylthio and ethylthio groups. Preferable examples of the aryl group include phenyl and substituted phenyl groups. Preferable examples of the lower alkoxycarbonylalkyl group include ethoxycarbonylethyl and methoxycarbonylethyl groups. Examples of the lower alkyl groups $R_1$ and $R_2$ include those having 1 to 6 carbon atoms. Preferable examples thereof include methyl, ethyl and n-propyl groups. Examples of the lower cycloalkylmethyl group $R_3$ include cyclopropylmethyl and cyclobutylmethyl groups.

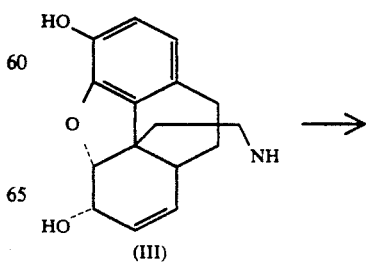

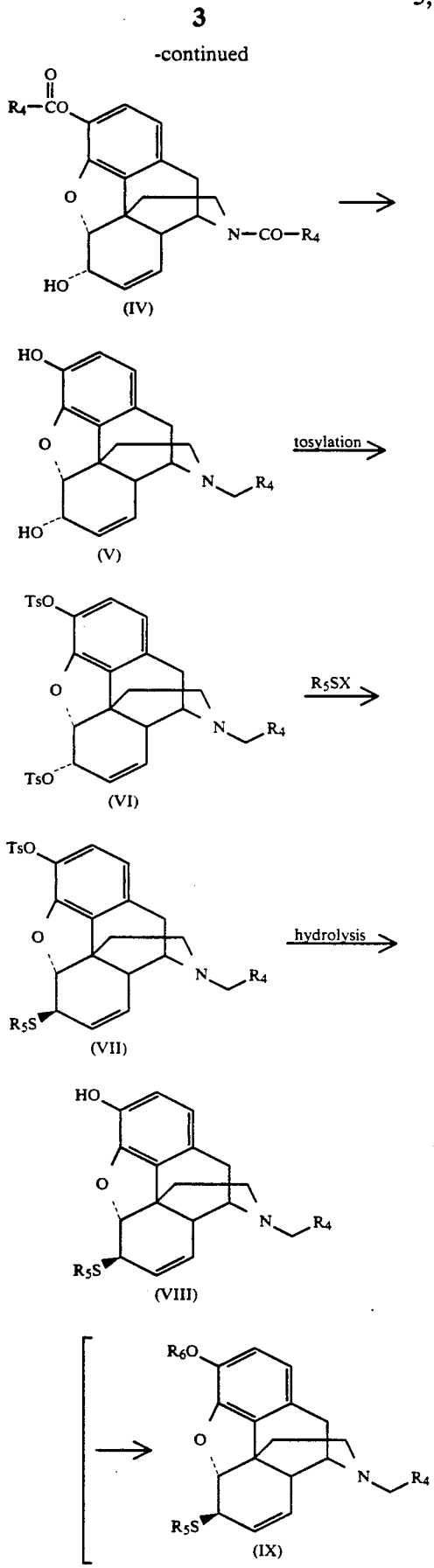

wherein
R₄ represents a lower cycloalkyl or a vinyl group;
R₆ represents a lower alkanoyl or a lower alkyl group;
TS represents a tosyl group; and
R₅ and X are as defined above.

Furthermore, the compound of the general formula (I) may be converted into an acid addition salt, if required. In order to form the acid addition salt for medical application, any pharmaceutically acceptable acid may be used without limitation. Examples of the acid include organic acids such as citric, fumaric, maleic and tartaric acids and mineral acids such as hydrochloric, hydrobromic, nitric and sulfuric acids.

As will be shown in Examples later, the compound of the present invention shows an intense analgesic activity approximately 5 to 6 times as high as that of morphine in a radiant heat-stimulation test using mice. Further, morphine shows scarcely any analgesic activity 3 hours after administration. In contrast thereto, the compound of the present invention still shows a significant analgesic activity after three hours, which indicates that it is superior to morphine in prolonged action. Furthermore, the compound of the present invention shows an excellent analgesic action via κ-receptor and a nonnarcotic action in μ-receptor in a transmural electric stimulation specimen of an extirpated guinea pig ileum piece. These facts suggest that it is highly effective as an analgesic.

Also, as will be shown in Examples given below, the compounds of the present invention showed analgesic effects exceeding those of morphine and pentazocine which were used as controls in a test with the use of mice. Furthermore, many of the compounds of the present invention showed excellent analgesic effects when orally administered. These facts indicate that they are excellent as analgesics.

Among the compounds of the present invention, the following ones are particularly preferable:

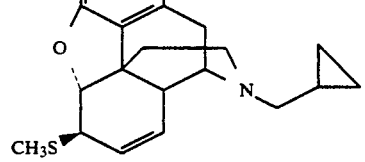

(X)

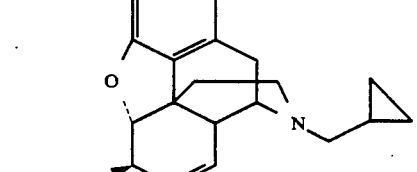

(XI)

These compounds are particularly excellent as medicines such as analgesics.

To further illustrate the present invention, the following Examples and Test Examples will be given.

EXAMPLE 1

6.35 ml of diisopropyl azodicarboxylate was added dropwise to 80 ml of a solution containing 8.46 g of triphenylphosphine in dry tetrahydrofuran at 0° C.

under a nitrogen gas stream. The obtained mixture was stirred under ice-cooling for 30 minutes. Next, 3.4 ml of thioacetic acid and a suspension of 5.0 g of cyclopropylmethylnormorphine, which had been synthesized from normorphine according to the method reported by Gates and Montzka, in dry tetrahydrofuran were added dropwise thereto under ice-cooling and the mixture was stirred for 4 hours. After distilling off the tetrahydrofuran, the residue was purified by silica gel column chromatography. Thus 3.9 g (yield: 66.2%) of 6β-acetylthio-N-cyclopropylmethylnormorphine and 1.0 g (yield: 15.3%) of 3-acetyl-6β-acetylthio-N-cyclopropylmethylnormorphine were obtained in the form of colorless crystals. 2.0 g of the 6β-acetylthio-N-cyclopropylmethylnormorphine was dissolved in tetrahydrofuran and a hydrogen chloride gas was introduced thereto. After distilling off the tetrahydrofuran, the residue was crystallized from ether. Thus 1.9 g of a hydrochloride of the following formula (VI) was obtained in the form of colorless crystals (m.p.: 192°-194° C.).

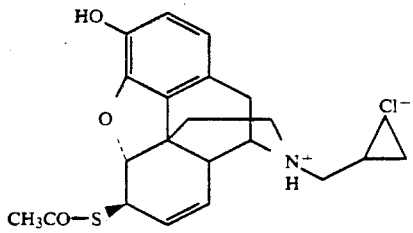
(VI)

Optical rotation $[\alpha]_D^{20}$: −259.9° (H₂O, C=0.297)
Elemental analysis as $C_{22}H_{25}NO_3S \cdot HCl$ (molecular weight: 419.969): calculated (%) C 62.92; H 6.24; N 3.34; found (%) C 62.72; H 6.18; N 3.14.

EXAMPLE 2

1.0 g of the 6β-acetylthio-N-cyclopropylmethylnormorphine obtained in Example 1 was dissolved in 2 ml of acetic anhydride and stirred at room temperature for 1 hour. Then ether was added and hydrogen chloride gas was introduced thereto. Thus 0.9 g of 3-acetyl-6β-acetylthio-N-cyclopropylmethylnormorphine hydrochloride of the formula (VII) was obtained in the form of colorless crystals. (m.p.: >200° C., slowly decomposed).

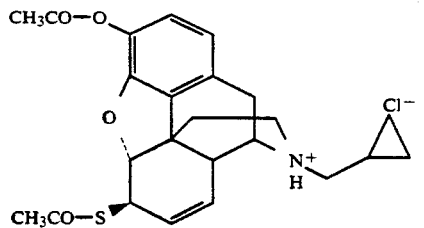
(VII)

Optical rotation $[\alpha]_D^{20}$: −260.2° (H₂O, C=0.327)
Elemental analysis as $C_{24}H_{27}NO_4S \cdot HCl$ (molecular weight: 462.007): calculated (%) C 62.39; H 6.11; N 3.03; found (%) C 62.12; H 6.25; N 2.87.

The 3-acetyl-6β-acetylthio-N-cyclopropylmethylnormorphine obtained in Example 1 was dissolved in ether and hydrogen chloride gas was introduced thereto. The hydrochloride thus obtained showed the same properties as those shown above.

EXAMPLE 3

Starting from 1.4 g of N-allylnormorphine, the procedure of Example 1 or 2 was repeated. Thus 0.9 g of 3-acetyl-6β-acetylthio-N-allylnormorphine hydrochloride of the formula (VIII) was obtained (m.p.: 207°-210° C.).

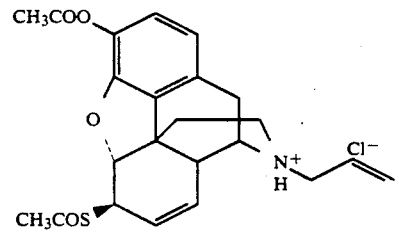
(VIII)

Optical rotation $[\alpha]_D^{25}$: −272.6° (H₂O, C=0.171)
Elemental analysis as $C_{23}H_{25}NO_4S \cdot HCl \cdot H_2O$ (molecular weight: 465.996): calculated (%) C 59.28; H 5.84; N 3.00; found (%) C 59.33; H 6.07; N 2.96.

EXAMPLE 4

1.6 g of the 6β-acetylthio-N-cyclopropylmethylnormorphine obtained in Example 1 was added to 50 ml of a 0.2N potassium hydroxide solution in ethanol. The obtained mixture was stirred under a nitrogen gas stream at room temperature for 30 minutes. The reaction mixture was then poured into a saturated aqueous solution of ammonium chloride and extracted with chloroform. The extract was dehydrated and concentrated under reduced pressure. Thus 6β-mercapto-N-cyclopropylmethylnormorphine was obtained. This product was reacted with 0.88 ml of propionyl chloride in chloroform in the presence of 1.4 ml of triethylamine. After 2 hours, the reaction mixture was washed with a saturated aqueous solution of sodium hydrogencarbonate and a saturated aqueous solution of common salt, dehydrated and concentrated under reduced pressure. The residue was purified by silica gel column chromatography (3% methanol/chloroform). Thus 1.2 g of 3-propionyl-6β-propionylthio-cyclopropylmethylnormorphine was obtained [mass spectrum (m/z): 453 (M)]. This product was converted into its hydrochloride of the formula (IX) in a conventional manner (m.p.: 202°-206° C.).

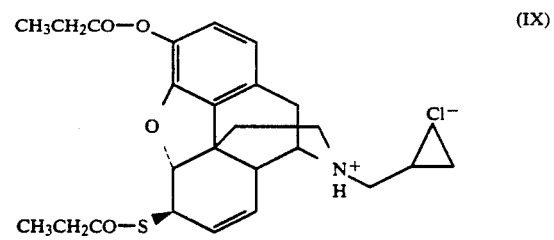
(IX)

Optical rotation $[\alpha]_D^{25}$: −252.88° (MeOH, C=0.200)

EXAMPLE 5

The procedure of Example 4 was repeated except that the propionyl chloride was replaced by isobutyl chloride. Thus 3-isobutylyl-6β-isobutylylthio-cyclopropylmethylnormorphine hydrochloride of the formula (X) was obtained at a yield of 75% (m.p.: 210°-215° C.).

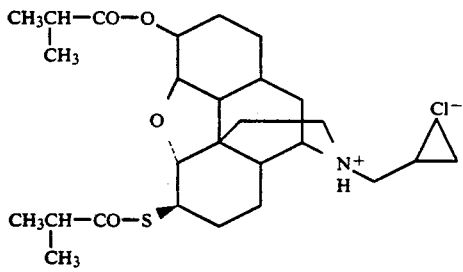

Optical rotation $[\alpha]_D^{25}$: −262.62° (MeOH, C=0.198)

EXAMPLE 6

Synthesis of 6β-methylthio-N-cyclopropylmethylnormorphine

To a solution of 3.0 g of cyclopropylmethylnormorphine-3,6-ditosylate, which had been obtained by tosylating cyclopropylmethylnormorphine in a conventional manner, in 15 ml of DMF, 4 ml of a 15% aqueous solution of methyl mercaptan sodium salt was added. The obtained mixture was stirred at room temperature for 3 hours. Then the reaction mixture was poured into a saturated aqueous solution of ammonium chloride, extracted with ethyl acetate, successively washed with a saturated aqueous solution of sodium hydrogencarbonate, water and a saturated aqueous solution of common salt and dehydrated over sodium sulfate anhydride. After distilling off the solvent, the residue was purified by silica gel chromatography to thereby give 2.0 g of 6β-methylthio-N-cyclopropylmethylnormorphine-3-tosylate. 2.0 g of this tosylate was hydrolyzed with 0.2N potassium hydroxide/ethanol and converted into hydrochloride. Thus 1.5 g of 6β-methylthio-N-cyclopropylnormorphine hydrochloride was obtained.

m.p.: 184°–186° C.

Specific rotation $[\alpha]_D = 240.0°$ (C=0.190, MeOH).

EXAMPLE 7

Synthesis of 3-acetyl-6β-methylthio-N-cyclopropylmethylnormorphine 1.5 g of 6β-methylthio-N-cyclopropylmethylnormorphine obtained in Example 6 was acetylated in acetic anhydride and a hydrogen chloride gas was bubbled into the reaction mixture. Thus 3-acetyl-6β-methylthio-N-cyclopropylmethylnormorphine hydrochloride was obtained quantitatively.

m.p.: 210°–215° C.

| Elemental analysis as $C_{23}H_{27}NO_3S \cdot HCl \cdot H_2O$ (M.W.: 451.998) | | | |
|---|---|---|---|
| | C | H | N |
| calculated (%) | 61.12 | 6.69 | 3.10 |
| found (%) | 60.82 | 6.72 | 3.08 |

EXAMPLE 8

Synthesis of 3-acetyl-6β-propylthio-N-cyclopropylmethylnormorphine

To a solution of 200 mg of sodium hydride, from which oily components had been removed, in 2 ml of DMF, 0.4 ml of propyl mercaptan was added under a nitrogen gas stream and the obtained mixture was stirred at room temperature for 30 minutes. Next, a solution of 1.5 g of N-cyclopropylmethylnormorphine-3,6-ditosylate in 5 ml of DMF was added thereto dropwise. After stirring at room temperature for 1 hour, the mixture was poured into a saturated aqueous solution of ammonium chloride and extracted with ethyl acetate. The extract was successively washed with a saturated aqueous solution of sodium hydrogencarbonate, water and a saturated aqueous solution of common salt and dried over sodium sulfate anhydride. After distilling off the solvent, the residue was purified by silica gel chromatography (2.5% methanol/chloroform) to thereby give 720 mg of 6β-propylthio-N-cyclopropylmethylnormorphine-3-tosylate. The obtained compound was treated in the same manner as those described in Examples 6 and 7. Thus 3-acetyl-6β-propylthio-N-cyclopropylnormorphine hydrochloride was obtained.

m.p.: 225°–228° C.

| Elemental analysis as $C_{25}H_{31}NO_3S \cdot HCl$ (M.W.: 462.052) | | | |
|---|---|---|---|
| | C | H | N |
| calculated (%) | 64.99 | 6.98 | 3.03 |
| found (%) | 64.75 | 6.99 | 2.98 |

EXAMPLE 9

Synthesis of 17-cyclopropylmethyl-7,8-didehydro-4,5α-epoxy-3-methoxy-6β-methylthiomorphinan Starting from 17-cyclopropylmethyl-7,8-didehydro-4,5α-epoxy-3-methoxymorphinan-6α-ol, the procedure of Example 6 was repeated to thereby give the title compound.

Specific rotation $[\alpha]_D = -263.44°$ (C=0.186, MeOH)

EXAMPLE 10

Synthesis of 3-acetyl-6β-methyldithio-N-cyclopropylmethylnormorphine 1.0 g of 3-acetyl-6β-acetylthio-N-cyclopropylmethylnormorphine was added to 40 ml of a 0.2N potassium hydroxide/ethanol solution containing 5 ml of a solution of methyl mercaptan in ethanol. After treating at room temperature for 30 minutes, a methyl disulfide compound was obtained. Then the procedure of Example 7 was repeated to thereby give 3-acetyl-6β-methyldithio-N-cyclopropylmethylnormorphine hydrochloride was obtained.

m.p.: 215°–217° C.

EXAMPLE 11

Synthesis of 3-acetyl-6β-phenylthio-N-cyclopropylmethylnormorphine

The procedure of Example 8 was repeated except that the propyl mercaptan was replaced with thiophenol. Thus 3-acetyl-6β-phenylthio-N-cyclopropylmethylnormorphine hydrochloride was obtained.

m.p.: 240°–245° C.

EXAMPLE 12

Synthesis of 3-acetyl-6β-isobutylthio-N-cyclopropylmethylnormorphine

The procedure of Example 8 was repeated except that the propyl mercaptan was replaced with isobutyl mercaptan. Thus 3-acetyl-6β-isobutylthio-N-cyclopropylmethylnormorphine hydrochloride was obtained.

m.p.: 214°-214°-215° C.

Specific rotation $[\alpha]_D = -251.92°$ (C=0.156, MeOH).

EXAMPLE 13

Synthesis of 3-acetyl-6α-ethoxycarbonylethylthio-N-cyclopropylmethylnormorphine The procedure of Example 8 was repeated to thereby give β-mercaptopropionic acid ethyl ester. Then the obtained product was esterified to thereby give 3-acetyl-6β-ethoxycarbonylethylthio-N-cyclopropylmethylnormorphine hydrochloride.

m.p.: 192°-194° C.

TEST EXAMPLE 1

Analgesic Examination by Radiant Heat-Stimulation Test

The compounds of the present invention and morphine hydrochloride were subcutaneously injected into male mice (Slc: ddy) aged 4 weeks. Each group had 7 animals. An hour after the injection, the analgesic effect of each compound was examined by radiant heat-stimulation test [refer to A. G. Hayes, M. J. Sheehan, M. B. Tyers; Brit. J. Pharmacol., 91, 111-115 (1987)]. Namely, the tail of each mouse was irradiated with intense light and the time required until the animal twitched its tail was measured. The value thus measured was referred to as the pain threshold. FIG. 1 shows the results.

The compounds (VI) and (VII) showed each an analgesic effect depending on dose within a range of from 0.03 to 1.0 mg/kg. The effects of both of these compounds were statistically significant at a dose of 1.0 mg/kg ($p<0.01$ in Dunnett's t-test).

On the other hand, the morphine hydrochloride employed as a control showed a significant analgesic effect at a dose of 3.2 mg/kg or above.

TEST EXAMPLE 2

Transmural Electric Stimulation Test on an Extirpated Guinea Pig Ileum Piece The effects of the compounds were examined by applying transmural electric stimulation (0.1 Hz) to extirpated guinea pig ileum pieces while using the smooth muscle contraction as an indication [refer to H. K. Kopsterlitz, A. A. Waterfield; Annu. Rev. Pharmacol., 15, 29-47 (1975)]. Table 1 shows the results.

The data shown in Table 1 were calculated according to a method reported by Arunlakshana and Schild [refer to O. Arunlakashana, H.O. Schild; Brit. J. Pharmacol., 14, 48-58 (1959)]. Each value is expressed in mean ± standard deviation.

TABLE 1

Transmural Electric Stimulation Test on an Extirpated Guinea Pig Ileum Piece

|  | pD | pA$_2$ (naloxone) | Slope |
|---|---|---|---|
| Morphine hydrochloride | 7.32 ± 0.13 | 8.45 ± 0.13 | (1.03 ± 0.09) |
| Compound VI | 8.38 ± 0.06 | 7.75 ± 0.12 | (0.93 ± 0.09) |
| Compound VII | 9.01 ± 0.16 | 7.80 ± 0.13 | (0.84 ± 0.11) |

TEST EXAMPLE 3

Analgesic Effect Evaluated by Acetic Acid-Writhing Test

The compounds of the present invention, morphine hydrochloride and pentazocine were subcutaneously administered to mice aged 5 weeks (Slc:ddy, male). Each group had 7 animals. After 30 minutes, 0.1 ml/10 g body weight of 0.6% acetic acid was intraperitoneally administered to the mice. After 10 minutes, the writhing number was counted within 10 minutes. Table 2 shows the ED$_{50}$ data thus obtained [refer to R. Koster, M. Anderson, E.I. Debeer; Fed. Proc., 18, 412 (1959) regarding the acetic acid-writhing test].

TABLE 2

| Ex. No. | Compound | ED$_{50}$ (mg/kg) |
|---|---|---|
| 2 | 3-acetyl-6β-acetylthio-N-cyclopropylmethylnormorphine hydrochloride | 0.062 |
| 3 | 3-propionyl-6β-propionylthio-N-cyclopropylmethylnormorphine hydrochloride | 0.047 |
| 7 | 3-acetyl-6β-methylthio-N-cyclo-propylmethylnormorphine hydrochloride | 0.012 |
| 8 | 3-acetyl-6β-propylthio-N-cyclopropylmethylnormorphine hydrochloride | 0.029 |
|  | 17-cyclopropylmethyl-7,8-didehydro-4,5α-epoxy-3-methoxy-6β-methyl thiomorphinan | 0.198 |
| 10 | 3-acetyl-6β-methyldithio-N-cyclopropylmethylnormorphine hydrochloride | 0.021 |
| Comparative | morphine hydrochloride | 0.139 |
| Comparative | pentazocine | 0.869 |

TEST EXAMPLE 4

Analgesic effect achieved by oral administration

The compound of the present invention and morphine hydrochloride were orally administered to mice aged 5 weeks (Slc:ddy, male). Each group had 7 animals. After 60 minutes, 0.1 ml/10 g body weight of 0.75% acetic acid was intraperitoneally administered to the mice. After 10 minutes, the writhing number was counted within 10 minutes. Table 3 shows the ED$_{50}$ data thus obtained.

TABLE 3

| Ex. No. | Compound | ED$_{50}$ (mg/kg) |
|---|---|---|
| 7 | 3-acetyl-6β-methylthio-N-cyclopropylmethylnormorphine hydrochloride | 5.29 |
| Comparative | morphine hydrochloride | 9.40 |

What is claimed is:

1. A compound represented by the following formula:

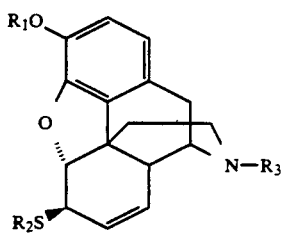

wherein
R₁ represents a hydrogen atom or a lower alkanoyl group;
R₂ represents a lower alkanoyl group; and
R₃ represents a cyclopropylmethyl or an allyl group, or a pharmaceutically acceptable acid addition salt thereof.

2. A pharmaceutical composition which comprises a compound represented by the following formula:

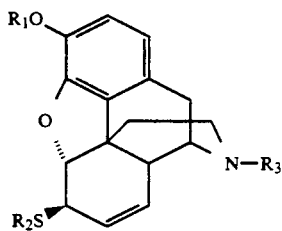

wherein
R₁ represents a hydrogen atom or a lower alkanoyl group;
R₂ represents a lower alkanoyl group and;
R₃ represents a cyclopropylmethyl or an allyl group, or a pharmaceutically acceptable acid addition salt thereof.

3. A method for relieving pain which comprises administering an effective amount of a compound represented by the following formula:

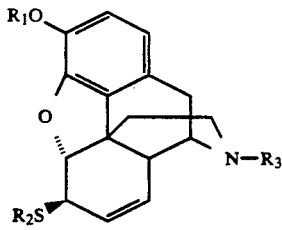

wherein
R₁ represents a hydrogen atom or a lower alkanoyl group;
R₂ represents a lower alkanoyl group; and
R₃ represents a cyclopropylmethyl or an allyl group, or a pharmaceutically acceptable acid addition salt thereof, to a man or an animal.

4. An anesthetic method which comprises administering to an animal or human an effective amount of a compound represented by the following formula:

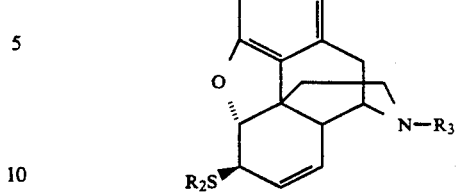

wherein
R₁ represents a hydrogen atom or a lower alkanoyl group;
R₂ represents a lower alkanoyl group; and
R₃ represents a cyclopropylmethyl or an allyl group, or a pharmaceutically acceptable acid addition salt thereof.

5. A compound of the formula:

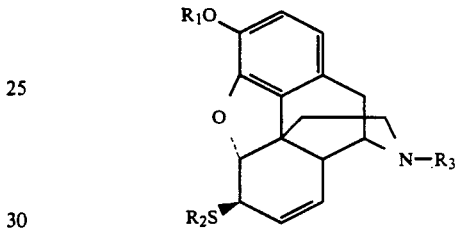

wherein
R₁ represents a hydrogen atom, a lower alkyl group or a lower alkanoyl group;
R₂ represents a lower alkyl group;
R₃ represents a lower cycloalkylmethyl group or an allyl group, or
a pharmaceutically acceptable acid addition salt thereof.

6. The compound as claimed in claim 5 of the formula

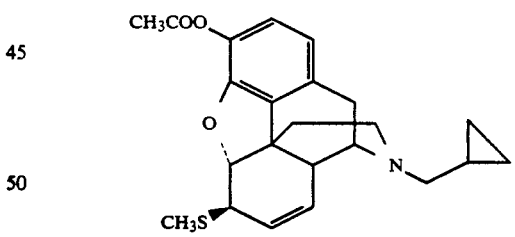

or a pharmaceutically acceptable acid addition salt thereof.

7. The compound as claimed in claim 5 of the formula:

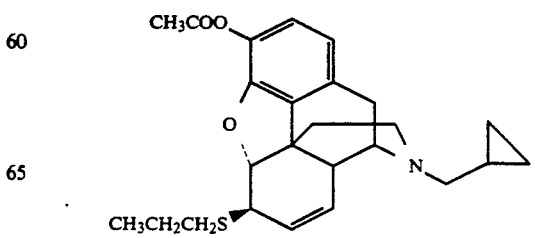

or a pharmaceutically acceptable acid addition salt thereof.

8. A compound according to claim 5 selected from the group consisting of 6β-methylthio-N-cyclopropylmethyl-normorphine; 3-acetyl-6β-methylthio-N-cyclopropylmethyl-normorphine; 3-acetyl-6β-propylthio-N-cyclopropylmethyl-normorphine; 17-cyclopropylmethyl-7,8-didehydro-4,5α-epoxy-3-methoxy-6β-methylthiomorphinan; and 3-acetyl-6β-isobutylthio-N-cyclopropylmethyl-normorphine.

9. A pharmaceutical composition which comprises a pharmaceutically acceptable amount of compound of the formula:

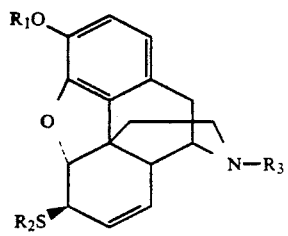

wherein
- $R_1$ represents a hydrogen atom, a lower alkyl group or a lower alkanoyl group;
- $R_2$ represents a lower alkyl group;
- $R_3$ represents a lower cycloalkylmethyl group or an allyl group, or
- a pharmaceutically acceptable acid addition salt thereof, together with a pharmaceutically acceptable excipient.

10. A method for relieving pain which comprises administering an effective amount of a compound of the formula:

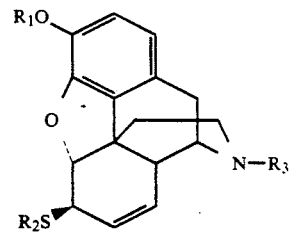

wherein
- $R_1$ represents a hydrogen atom, a lower alkyl group or a lower alkanoyl group;
- $R_2$ represents a lower alkyl group;
- $R_3$ represents a lower cycloalkylmethyl group or an allyl group, or
- a pharmaceutically acceptable acid addition salt thereof to a human or an animal.

11. An anesthetic method which comprises administering an effective amount of a compound of the formula:

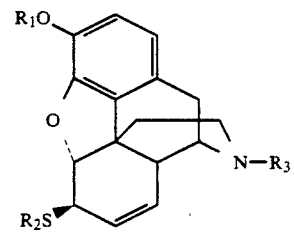

wherein
- $R_1$ represents a hydrogen atom, a lower alkyl group or a lower alkanoyl group;
- $R_2$ represents a lower alkyl group;
- $R_3$ represents a lower cycloalkylmethyl group or an allyl group, or
- a pharmaceutically acceptable acid addition salt thereof to a human or an animal.

* * * * *